United States Patent [19]

Schuster

[11] 4,203,520
[45] May 20, 1980

[54] RECEPTACLE FOR RECEIVING ARTICLES FOR STORAGE IN STERILIZED CONDITION

[76] Inventor: Samuel J. Schuster, 617 Vallombrosa, Pasadena, Calif. 91107

[21] Appl. No.: 937,213

[22] Filed: Aug. 28, 1978

[51] Int. Cl.² .............................................. B65D 33/16
[52] U.S. Cl. ....................................... 206/439; 229/62
[58] Field of Search ................. 206/439, 484.1, 363, 206/364, 365; 229/65

[56] References Cited

U.S. PATENT DOCUMENTS

| | | | |
|---|---|---|---|
| 3,088,255 | 5/1963 | Griem | 206/439 |
| 3,246,959 | 4/1966 | Bremer | 206/439 |
| 3,472,369 | 10/1969 | Schuster | 206/439 |
| 3,754,700 | 8/1973 | Bonk | 206/439 |
| 3,761,013 | 9/1973 | Schuster | 206/439 |
| 3,819,106 | 6/1974 | Schuster | 206/439 |
| 4,057,144 | 11/1977 | Schuster | 206/439 |

Primary Examiner—Herbert F. Ross
Attorney, Agent, or Firm—Fraser and Bogucki

[57] ABSTRACT

A receptacle for medical articles or the like is disclosed and includes confronting walls of impermeable, polymeric films portions of which sandwich a membrane impermeable to bacteria and other microorganisms but comparatively highly permeable to sterilizing vapor. The membrane is bonded to the receptacle walls so as to define with the walls a tortuous path aiding in the prevention of entry of contaminating microorganisms. The entire membrane is interposed between the walls so that virtually all surfaces of the membrane are protected against contamination. Various wall-to-membrane sealing configurations are disclosed.

29 Claims, 10 Drawing Figures

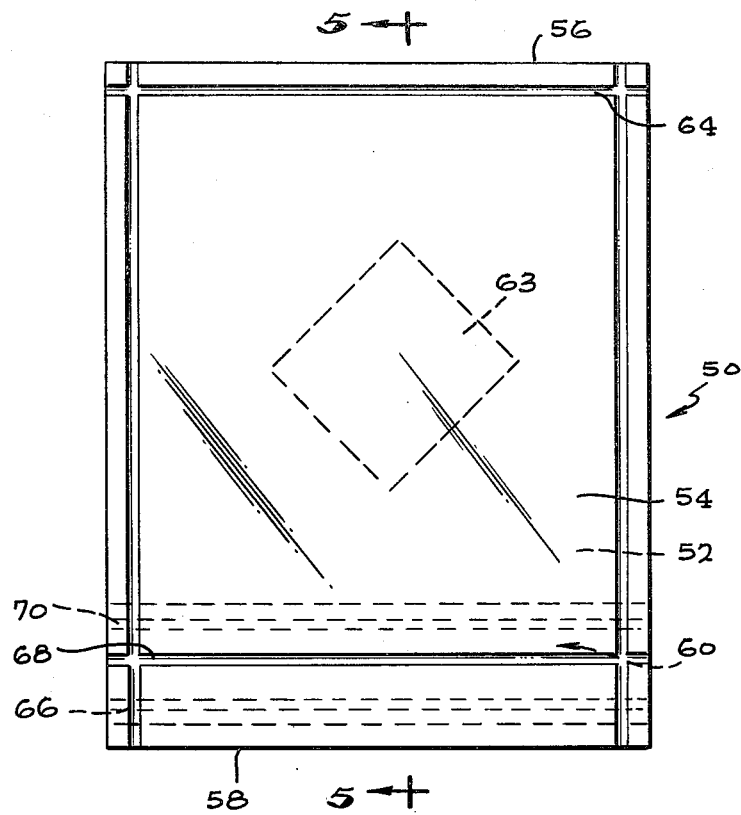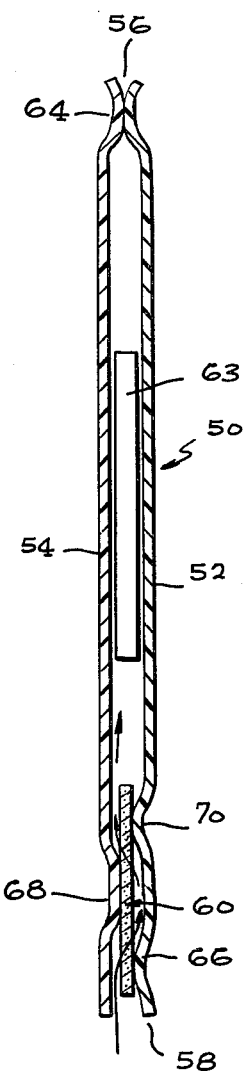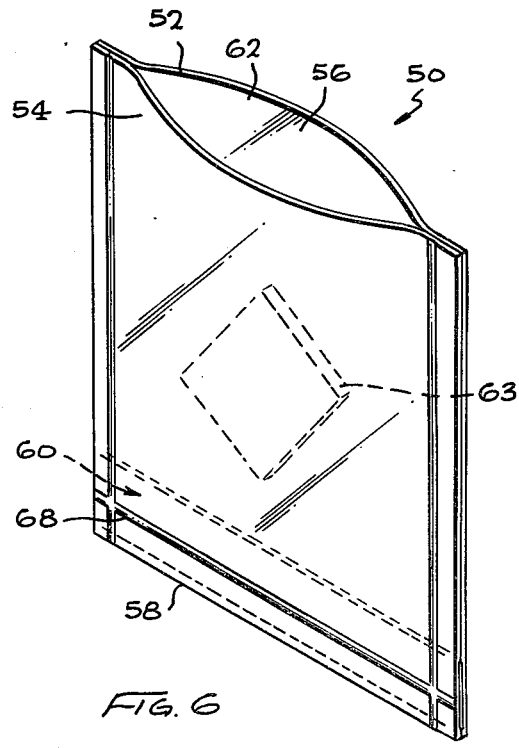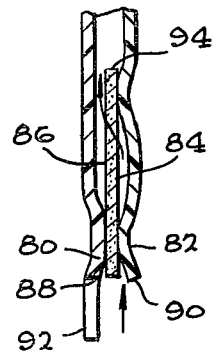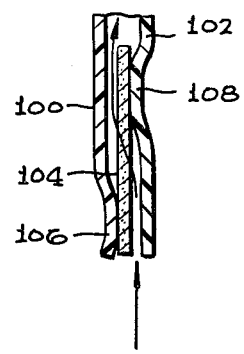

RECEPTACLE FOR RECEIVING ARTICLES FOR STORAGE IN STERILIZED CONDITION

FIELD OF THE INVENTION

The present invention relates to packaging techniques and more particularly to improvements in receptacles of the type having a membrane impermeable to bacteria and other contaminating microorganisms but highly permeable to sterilizing vapors.

BACKGROUND OF THE INVENTION

There is an increasing need for sterilizable packaging, particularly for medical appliances and supplies, providing an exceedingly high degree of assurance against contamination of the enclosed article. The sterility of heart valves or like prosthetic devices, for example, simply cannot be open to question.

Known receptacles for receiving medical articles and storing those articles in sterilized condition typically comprise a bag of flexible thermoplastic or thermosetting material having an access opening sealed with a membrane that is permeable to sterilizing vapor. Because the closure membrane is secured to the outside surfaces of the bag, large portions of the membrane are exposed to the surrounding environment. Direct impingement on those surface areas of bacteria-carrying dust particles, for example, can lead to contamination of the contents of the package. In addition, storage of the package in a humid atmosphere can lead to the germination of mold spores that can grow through the membrane. The very characteristics that make the membrane usable for a sterilization process render it vulnerable to capillary transfer of moisture across its thickness. Microorganisms can grow on the outside surface of a moist membrane and transfer through to the inside surface even though the membrane pore size may be too small for permeation of airborne bacteria.

Moreover, the removal of a sterile item from known packages often results in contact with a nonsterile edge or other portion of the package, most notably the exterior of the package which is not protected.

SUMMARY OF THE INVENTION

A receptacle in accordance with one exemplary form of the present invention comprises a pair of confronting, impermeable, polymeric films or walls portions of which sandwich a membrane highly permeable to sterilizing vapor. The membrane is bonded to the inside surfaces of the walls so that with an article enclosed and the receptacle completely sealed, a tortuous path is defined between the exterior and interior of the receptacle through the portion of the receptacle incorporating the membrane.

By interposing the vapor-permeable membrane between the walls of the receptacle several important advantages are realized. Virtually all surfaces of the membrane are protected against contamination. The tortuous path that must be followed into or out of the interior of the bag, combined with the mechanical filtering properties of the membrane, provide a formidable, superior barrier against the passage of contaminating microorganisms.

Removal of the article may be accomplished by "dumping" rather than by having to reach into the receptacle through an access opening. The risk of contamination is thereby reduced by eliminating some of the handling of the article and decreasing the possibility of contact with nonsterile surfaces.

Moreover, interposition of the membrane between the walls of the receptacle provides important advantages in the fabrication of the receptacle and the materials used. For example, where the receptacle is made of heat sealable materials, all heat seals are applied through the walls to the membrane (typically a better insulator than the wall material) rather than vice versa thus reducing the heat sealing dwell time. Also, the use of thick films, for example, 6 to 12 mils, thereby becomes feasible. The differential thermal characteristics of the membrane and walls may moreover be used to advantage to facilitate application of a closure seal.

Not only can various polymeric films, such as polyethylene or polypropylene be used by themselves for the walls of the receptacle, but a wide range of laminated films becomes available to impart specific properties to the outer surface, such as strength, wear resistance, and so forth, since the sealing characteristics of the outer surface are no longer a consideration.

BRIEF DESCRIPTION OF THE DRAWINGS

Further objects, advantages and features of the present invention will become readily apparent from a reading of the detailed description in conjunction with the accompanying drawings in which:

FIG. 4 is a front view of a receptacle constructed pursuant to an alternative embodiment of the present invention;

FIG. 5 is a cross-section view of the receptacle of FIG. 4 as seen along 5—5;

FIG. 6 is a perspective view of the receptacle shown in FIGS. 4 and 5;

FIG. 7 shows, in cross-section, a portion of a receptacle in accordance with another embodiment of the present invention;

FIG. 8 is a cross-sectional view of a portion of a receptacle in accordance with yet another embodiment of the present invention.

DETAILED DESCRIPTION OF THE PREFERRED EMBODIMENTS

At the outset, it is to be noted that in the accompanying drawings the thicknesses of the materials from which the receptacle is fabricated have been greatly exaggerated to clearly show their interrelationships.

Figure 1:
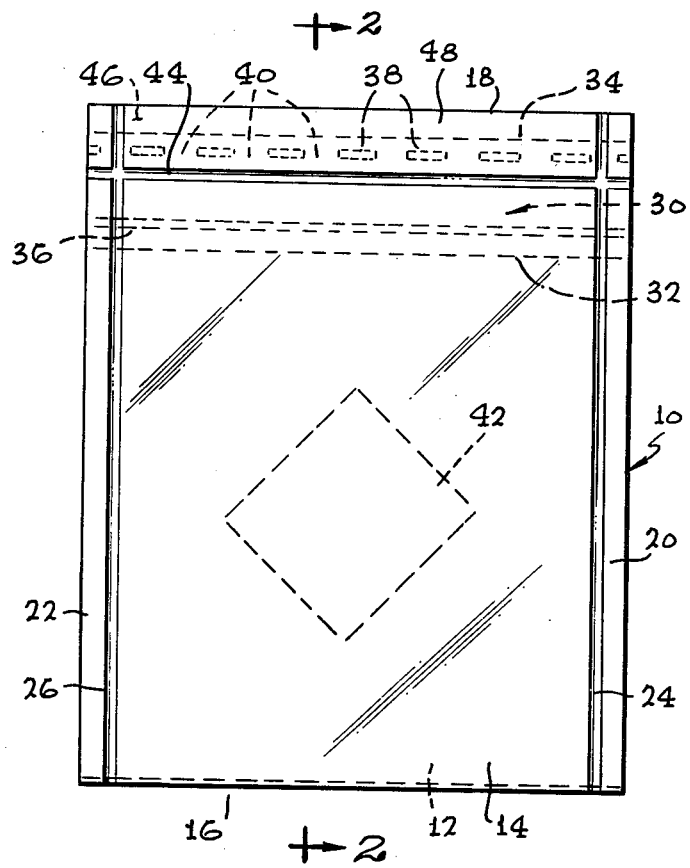
FIG. 1 is a front view of a receptacle constructed pursuant to the teachings of the present invention.
Figures 2, 2A:
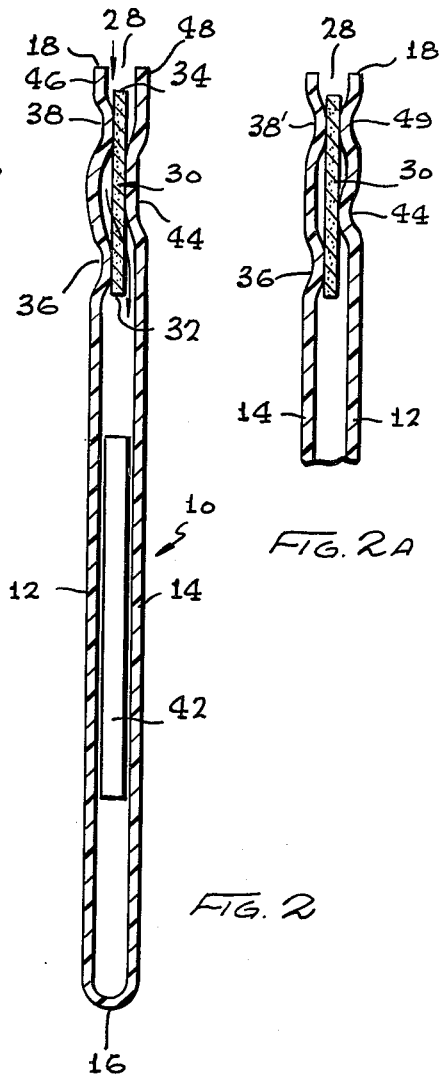
FIG. 2 is a cross-section view of the bag of FIG. 1 as seen along 2—2.
FIG. 2A is a cross-section view of a portion of the bag of FIGS. 1 and 2 following application of final closure seals.
Figure 3:
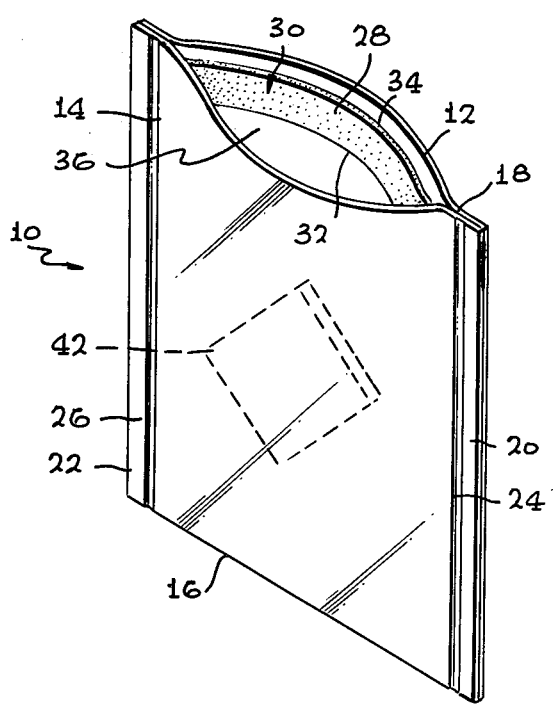
FIG. 3 is a perspective view of the receptacle of FIGS. 1 and 2.

Referring to FIGS. 1-3, there is shown a receptacle 10 according to one form of the present invention. A rectangular, polymeric film, sufficiently thick to provide the desired impermeability to both sterilizing vapor and to bacteria and other microorganisms, is folded to define a pair of confronting walls 12 and 14 having a periphery comprising a first, transverse end 16 along the fold line, a transverse end 18 opposite the first end and longitudinal edge portions 20 and 22. Continuous heat seal joinder lines 24 and 26 bond the walls together along the longitudinal edge portions 20 and 22, respectively. Thus, the receptacle so far described is completely closed except for an opening 28 in the part of the transverse end 18 extending between the longitudinal seals 24 and 26.

The receptacle 10 further includes a membrane 30 sandwiched between the confronting walls 12 and 14 adjacent the opening 28. The membrane 30 is preferably in the form of a transversely oriented strip extending the entire width of the receptacle and joined to the walls by portions of the longitudinal edge seals 24 and 26. The strip can be narrow so that it occupies only a small area relative to the overall area of the receptacle thereby providing an unobstructed view of the enclosed article through either face of the receptacle when transparent film is used, and significantly reducing per unit material costs.

The membrane 30 is typically made of a material such as paper or "Tyvek" (a spun polyolefin of the duPont Company) that is impermeable to bacteria and other microorganisms but highly permeable, in comparison to the remainder of the receptacle, to sterilizing vapors such as steam or ethylene oxide.

Preferably, the membrane 30 is disposed in its entirety within the confines of the walls so that no part of the membrane projects from the opening 28. Protection against the contamination of the membrane, among other advantages to be described, is thereby afforded.

Figure 9:
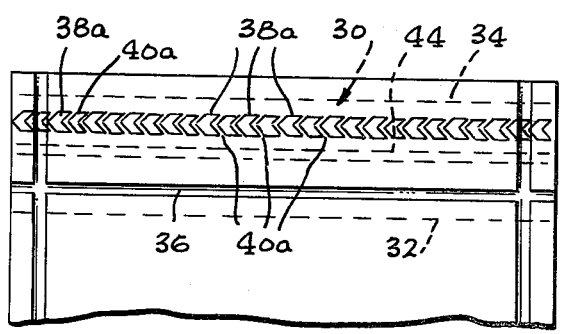
FIG. 9 is a front view of a portion of a receptacle in accordance with another, alternative embodiment of the present invention.

The membrane 30 has an inner edge 32 adjoining the interior of the receptacle and an outer edge 34 adjacent the opening 28. The membrane 30 is secured to the wall 12 by a continuous, transverse seal 36 along the inner edge 32 and by an intermittent, transverse seal, consisting of a series of aligned, individual seals 38 extending along the outer edge 34. The seals 38 define between them a series of sterilizing vapor passages 40. The seals 38 may be of generally rectangular shape, as is the case of the embodiment shown in FIGS. 1–3, or alternatively, they may be configured and disposed relative to each other to define labyrinthine passages to further impede the ingress of contaminating microorganisms. An example of such an alternative configuration and disposition is shown in FIG. 9 in which closely spaced, chevron-shaped seals 38a define correspondingly shaped vapor passages 40a.

Referring specifically to FIG. 3, an article 42 to be stored in sterile condition is inserted into the receptacle through the opening 28. The opening is then sealed by a continuous, transverse closure seal 44 applied through the wall 14 to the membrane 30. The closure seal 44 is positioned outwardly of the seal 36 thereby defining a membrane breathing area bounded by the seals 36, 44 and by the longitudinal edge seals 24 and 26. The closure seal 44 is preferably made to be peelable and in this connection any of a variety of techniques known to those skilled in the art may be employed. For example, where the membrane 30 is made of paper, an appropriate coating may be provided. Since the closure seal 44 is applied through the wall 14 to the membrane 30, the temperature-time-pressure parameters are not particularly critical and the insulating qualities of the membrane prevents sealing of the membrane to the other wall 12. The placement of the closure seal, which will typically be applied by a medical product supplier intermediate the manufacturer of the receptacle and the ultimate user, can be indicated by printing appropriate indicia on the surface of the membrane 30 adjacent the wall 14, or on the wall itself.

After application of the closure seal 44, the interior of the package, including the enclosed article, is sterilized by the admission and subsequent purging of the sterilizing vapor in accordance with any of the various well known vapor sterilization processes. In the embodiments of FIGS. 1–3 and 9, the vapor flows through the passages 40 or 40a between the intermittent seals 38 and 38a, the space between the membrane 30 and the wall, 12 and through the breathing area of the membrane between the seals 36 and 44. The path between the opening 28 and the interior of the receptacle is therefore somewhat tortuous providing the advantages already described.

Opening of the receptacle 10 is best accomplished by grasping the extended margins 46 and 48 of the walls 12 and 14, respectively, and pulling back on the margin 48 to peel the wall 14 from the membrane. The article may be dumped through the opening thus provided while the portions of the wall adjacent the opening are maintained in a folded back condition so that contact between the article and nonsterilized surfaces is avoided.

If desired, final seals can be applied following the sterilization process to completely seal the membrane while retaining the ability to easily open the receptacle. Such final seals are shown in FIG. 2A. A continuous, transverse seal 38' is applied over the intermittent seals 38 to close off the passages 40. Another continuous, transverse seal 49 is applied in registration with the seal 38' to join the margin of the wall 14 adjacent the end 18 to the membrane 30. The seals 38' and 49 may be conveniently formed simultaneously by opposed heat seal jaws. Although disclosed in detail only in connection with the embodiment of FIGS. 1–3, it will become evident that the final sealing technique is applicable to the other embodiments of the invention and allows a very long shelf life with virtually absolute protection.

Turning now to FIGS. 4–6, the receptacle 50 shown therein includes walls 52 and 54, transverse ends 56 and 58 and a membrane 60. This embodiment is distinguishable from the previously described form of the invention principally in that the transverse end 56, opposite the end 58 incorporating the membrane 60, is provided with the opening, identified by the reference numeral 62 in FIG. 6, for receiving the article. The receptacle walls 52, 54 therefore comprise individual, confronting films. One advantage of this construction is that all of the transverse seals joining the walls and the membrane may be made as part of the manufacturing process where optimum control can be exercised over the temperature-time-pressure parameters of this sealing operation. After loading of the article 63 through the opening 62, as shown in FIG. 6, a transverse closure seal 64 is applied to join the two walls of the receptacle along the transverse end 56.

The embodiment of FIGS. 4–6 also illustrates an alternative membrane seal configuration in which all three seals, here identified by the reference numerals 66, 68 and 70, are continuous. The seals 66, 68 and 70 are staggered in the longitudinal direction so that the entering sterilizing vapor first passes between the wall 54 and the membrane 60, through the portion of the membrane defined by the seals 66 and 68, into the space between the membrane 60 and the walls 52, through another portion of the membrane 60 bounded by seals 66 and 70, and from there into the receptacle interior. A dual breathing area and microorganism barrier is thereby provided and the path leading into the interior of the receptacle is additionally tortuous thereby decreasing even further the chances of entry of contaminating microorganisms. Also as a result of this sealing configuration, somewhat thinner membrane material may be used facilitating the membrane-to-wall seals.

Opening of the package made in accordance with the embodiment of FIGS. 4-6 can be the same as already described in connection with the first embodiment, or, alternatively, the seal 64 at the transverse end 56 can be made peelable and the article removed from that end. Various other opening techniques will suggest themselves to those skilled in the art including the provision of a transverse line of notches in the surface of one or both walls positioned, for example, near the end 56. The receptacle is then opened by tearing the end of the package off along the notched line.

Further assurance against contact between the article and nonsterile surfaces can be provided by reducing to the greatest extent possible the length of the margins of the walls extending outwardly of the membrane. For example, as shown in FIG. 7, transverse wall-to-membrane seals 80 and 82 are positioned closely adjacent the outer edge 86 of the membrane 84, the outer edge 86 lying essentially flush with the outer edges 88, 90 of the walls. Seal 80 is continuous while seal 82 is intermittent. A tab 92 extending from the edge 88 aids in opening the receptacle. FIG. 7 also shows an inner, continuous transverse seal positioned at the inner edge 94 of the membrane so that this edge cannot catch the article as it is dumped from the receptacle.

FIG. 8 shows another embodiment of the invention that eliminates one of the wall-to-membrane seals. The receptacle of FIG. 8 includes walls 100, 102 and a membrane 104. The membrane is joined to the wall 100 by an outer, continuous transverse seal 106 and to the wall 102 by an inner, continuous transverse seal 108. The vapor path is similar to that described in connection with the embodiment of FIGS. 1-3. The membrane 104 is preferably made as narrow as possible to minimize nonsterile surface areas.

The present invention makes possible the use of a great variety of materials. The receptacle walls, for example, may be made of polyethylene or other thermoplastic film or laminations of thermoplastic film to such substances as mylar, nylon, polypropylene or paper. The outer laminate can be chosen for any desired properties including, for example, strength and wear resistance. The walls can be transparent to facilitate inspection and identification of the contents of the package or translucent, opaque or tinted. Tinting may be desirable in certain instances to control the entry of electromagnetic radiation in both the visible and non-visible portions of the spectrum. In case the atmosphere within the receptacle must be controlled, by way of a nitrogen flush or through the introduction of perservative gases such as formaldehyde or carbon dioxide, then materials such as laminations consisting of mylar, aluminum foil and polyethylene can be used.

The membrane may be fabricated of uncoated paper, in which case the inside surface of the receptacle is corona-treated to effect or improve the bond between the paper and receptacle walls, or paper with a peelable heat seal coating on one or both sides to allow the receptacle to be opened in a clean manner without the generation of fibers. Depending upon particular needs, other materials, both woven and nonwoven, that are impermeable to bacteria yet comparatively highly permeable to sterilizing vapors may be used. These alternatives include various paper-like materials such as Tyvek, already mentioned, or glass fiber products.

The bonds between the walls of the receptacle and between the walls and the membrane that are described above are preferably and most easily obtained by heat sealing but they may also be provided by adhesive or other forms of chemical or mechanical bonding.

Thus, the present invention may be embodied in other specific forms without departing from the spirit and the essential characteristics of the invention. The described embodiments are, therefore, to be considered in all respects as illustrative, the scope of the invention being defined by the appended claims rather than the foregoing description, and all modifications which come within the meaning and range of the claims or their equivalents are, therefore, intended to be embraced therein.

What is claimed is:

1. A receptacle for receiving articles for storage in sterilized condition, the receptacle being closed except for an opening for inserting the article, the receptacle comprising facing walls of material impermeable to both sterilizing vapor and microorganisms, and a substantially flat membrane impermeable to microorganisms but highly permeable to sterilizing vapor, the membrane being disposed between the facing walls in parallel relationship thereto, a portion of one surface of the membrane being bonded to at least one of the walls, the membrane being operatively associated with the walls to transfer sterilizing vapor to and from the interior of the receptacle along a path that traverses the surfaces of said membrane following insertion of the article and sealing of the opening by bonding a portion of the other side surface of the membrane to the other wall.

2. A receptacle as set forth in claim 1, in which the receptacle has a pair of opposite ends, the membrane being disposed adjacent one end, the opening being defined by the other end.

3. A receptacle as defined in claim 1, in which the receptacle has an end defining the opening, the membrane being disposed adjacent said end.

4. A receptacle as defined in claim 1, in which the membrane is bonded to the one wall with at least one continuous seal.

5. A receptacle as defined in claim 4, in which the membrane is bonded to the one wall with two, spaced-apart, continuous seals, the other portion of the membrane that is adapted to be bonded to the other wall being disposed between the two continuous seals.

6. A receptacle, as defined in claim 4, in which the membrane is bonded to the one wall with an intermittent seal proximate the receptacle opening and a continuous seal remote from the receptacle opening.

7. A receptacle, as defined in claim 6, in which the intermittent seal comprises a series of individual seals configured to define labyrinthine passages between the membrane and the one wall.

8. A receptacle for receiving articles for storage in sterilized condition, the receptacle having a periphery and an opening along the periphery for inserting the article, the remainder of the periphery being sealed, the receptacle comprising facing walls of material impermeable to both sterilizing vapor and microorganisms and a substantially flat membrane impermeable to microorganisms but highly permeable to sterilizing vapor, the membrane forming a portion of the closure of the receptacle, substantially the entire membrane being disposed between the facing walls in parallel relationship thereto, a portion of one side of the membrane being sealingly bonded to one of the walls and a portion of the other side surface of membrane being sealingly bonded to the other of the walls, the membrane being operatively associated with the walls to transfer sterilizing vapor to and from the interior of the receptacle along a path that traverse the side surfaces of said membrane following insertion of the article and sealing of the receptacle opening.

9. A receptacle, as defined in claim 8, in which at least one of the sealing bonds is separable to facilitate opening of the receptacle.

10. A receptacle, as defined in claim 8, in which the membrane is bonded to the one wall with two spaced-apart, continuous seals, and bonded to the other wall with a third continuous seal disposed between the two, spaced-apart seals.

11. A receptacle, as defined in claim 8, in which the membrane is bonded to the one wall with an intermittent seal remote from the interior of the receptacle and a continuous seal proximate the interior of the receptacle, and bonded to the other wall with a continuous seal.

12. A receptacle, as defined in claim 11, in which the intermittent seal comprises a series of individual seals configured to define labyrinthine passages between the membrane and the one wall.

13. A receptacle for receiving articles for storage in sterilized condition, said receptacle having opposed, longitudinal edge portions and opposed, transverse ends and including a pair of confronting walls of a material impermeable to both sterilizing vapor and microorganisms, the walls being sealed along the longitudinal edge portions and along one of the transverse ends, an opening being defined along the other transverse end, the receptacle further including a transversely-oriented, flat strip impermeable to microorganisms but highly permeable to sterilizing vapor extending the width of the receptacle near the opening and being parallel to and disposed substantially entirely between the walls of the receptacle, the strip having an outer, transversely oriented edge adjacent the opening and an inner, transversely oriented edge remote from the opening, on side surface of the strip being bonded to one of the walls by a first, continuous, transverse sealing joinder line, the opening of the receptacle being adapted to be sealed by a second continuous, transverse sealing joinder line in staggered relationship with the first joinder line bonding the other side surface of said strip to the other wall, the area of the strip bounded by the first and second joinder lines and the sealed longitudinal edge portions thereby defining a breathing area.

14. A receptacle, as defined in claim 13, in which the strip is joined to the one wall by a third, transverse sealing joinder line comprising a series of spaced individual seals.

15. A receptacle, as defined in claim 14, in which the spaced, individual seals are shaped to define labyrinthine passages between the seals and receptacle walls.

16. A receptacle, as defined in claim 14, in which the outer edge of the strip and the second and third transverse seals are positioned immediately adjacent said other transverse end of the receptacle and at least one of the walls includes a tab projecting outwardly from the other transverse end to facilitate opening of the receptacle.

17. A receptacle, as defined in claim 13, in which the strip is joined to the one wall by a third, continuous, transverse sealing joinder line in staggered relationship with the second joinder line thereby defining a second breathing area bounded by the second and third joinder lines and the sealed, longitudinal edge portions.

18. A receptacle, as defined in claim 13, in which the walls are formed of a single piece of polymeric film folded along said one transverse end.

19. A receptacle for receiving articles for storage in sterilized condition, said receptacle having opposed, longitudinal edge portions and opposed, transverse ends and including a pair of confronting walls of a material impermeable to both sterilizing vapor and microorganisms, the receptacle being closed along the longitudinal edge portions and along one of the transverse ends, an opening being defined along the outer transverse end, the receptacle further including a transversely oriented, flat strip impermeable to microorganisms but highly permeable to sterilizing vapor extending the width of the receptacle along the one transverse end and forming the closure of that end, the strip being disposed in substantially its entirety between the walls of the receptacle and parallel thereto and having an inner transverse edge proximate the interior of the receptacle and an outer transverse edge, one side surface of the strip being bonded to one of the walls by a first, continuous, transverse sealing joinder line and the other side surface of the strip being bonded to the other wall by a second, continuous, transverse sealing joinder line, the first and second joinder lines being staggered to define, with the closed longitudinal edge portions, a breathing area along the strip, the receptacle being adapted to be sealed along the other transverse end following insertion of articles.

20. A receptacle, as defined in claim 19, in which at least one of the joinder lines is separable to facilitate opening of the receptacle.

21. A receptacle, as defined in claim 19, in which the strip is bonded to the one wall by a third transverse sealing joinder line comprising a series of spaced, individual seals.

22. A receptacle, as defined in claim 21, in which the spaced, individual seals are shaped to define labyrinthine passages.

23. A receptacle, as defined in claim 19, in which the strip is bonded to the one wall by a third, continuous, transverse sealing joinder line in staggered relationship with the second joinder line to define a second breathing area bounded by the second and third joinder lines and the closed longitudinal edge portions.

24. A package for storing an article in sterilized condition comprising facing walls of material impermeable to both sterilizing vapor and microorganisms, the walls being bonded together along a periphery to define an interior enclosing the article, a portion of the peripheral bonding of the walls comprising a flat breathable membrane impermeable to microorganisms but highly permeable to sterilizing vapor, the membrane being disposed between the facing walls in parallel relationship thereto, one of the side surfaces of said membrane being bonded to one of the walls by a first, continuous sealing joinder line and the other side surface of said membrane being bonded to the other wall by a second, continuous sealing joinder line, the first and second joinder lines being positioned to define a breathing area transversing the side surface of said membrane.

25. A package, as defined in claim 24, in which at least one of the joinder lines is peelable to facilitate opening of the package.

26. A package, as defined in claim 24, in which the membrane is bonded to the one wall by a third sealing joinder line comprising a series of spaced, individual seals.

27. A package, as defined in claim 26, in which the spaced, individual seals are shaped to define labyrinthine passages.

28. A package, as defined in claim 24, in which the membrane is bonded to the one wall by a third, continuous sealing joinder line positioned relative to the second joinder line to define with the second line a second breathing area along the membrane.

29. A package, as defined in claim 24, which includes means bonding the membrane to at least one of the walls for finally sealing the package and substantially completely sealing the membrane between the walls.

* * * * *

UNITED STATES PATENT AND TRADEMARK OFFICE
CERTIFICATE OF CORRECTION

PATENT NO. : 4,203,520

DATED : May 20, 1980

INVENTOR(S) : Samuel J. Schuster

It is certified that error appears in the above-identified patent and that said Letters Patent are hereby corrected as shown below:

Column 4, line 9, after "38", "and" should read --or--. Column 5, line 56, after "of" and before "gases", "perservative" should read --preservative--. Column 6, line 28, after "one" and before "surface", insert --side--. Column 7, line 2, after "side" and before "of" (second occurrence), insert --surface--; line 39, after "being" and before "parallel", insert --disposed--; line 40, before "substantially", strike "disposed"; line 43, after "opening," and before "side", "on" should read --one--. Column 8, line 15, after "the" and before "transverse", "outer" should read --other--.

Signed and Sealed this

Nineteenth Day of August 1980

[SEAL]

Attest:

SIDNEY A. DIAMOND

Attesting Officer

Commissioner of Patents and Trademarks